US012685658B2

(12) United States Patent　　(10) Patent No.: US 12,685,658 B2

Savard et al.　　(45) Date of Patent: *Jul. 21, 2026

(54) ORTHOTIC FOOT BRACE AND METHOD OF ASSEMBLY THEREOF

(71) Applicant: ORTHÈSES TURBOMED INC. / TURBOMED ORTHOTICS INC., Saint-Augustin-de-Desmaures (CA)

(72) Inventors: Stéphane Savard, Québec (CA); François Côté, Lévis (CA)

(73) Assignee: ORTHÈSES TURBOMED INC., Saint-Augustin-de-Desmaures (CA)

( * ) Notice: Subject to any disclaimer, the term of this patent is extended or adjusted under 35 U.S.C. 154(b) by 225 days.

This patent is subject to a terminal disclaimer.

(21) Appl. No.: 18/707,098

(22) PCT Filed: Dec. 15, 2022

(86) PCT No.: PCT/CA2022/051826

§ 371 (c)(1),
(2) Date: May 2, 2024

(87) PCT Pub. No.: WO2023/108280

PCT Pub. Date: Jun. 22, 2023

(65) Prior Publication Data

US 2025/0025325 A1　　Jan. 23, 2025

Related U.S. Application Data

(60) Provisional application No. 63/289,675, filed on Dec. 15, 2021.

(51) Int. Cl.
*A61F 5/01* (2006.01)

(52) U.S. Cl.
CPC .................................. *A61F 5/0113* (2013.01)

(58) Field of Classification Search
CPC .... A61F 5/0113; A61F 5/0111; A61F 5/0104; A61F 5/0102; A61F 5/01; A61F 5/00;
(Continued)

(56) References Cited

U.S. PATENT DOCUMENTS

| 4,938,777 A | 7/1990 | Mason et al. |
| 8,529,484 B2 | 9/2013 | Savard |

(Continued)

FOREIGN PATENT DOCUMENTS

| CN | 110013423 A | 7/2019 |
| WO | 2011097723 A1 | 8/2011 |

(Continued)

*Primary Examiner* — Tarla R Patel

(74) *Attorney, Agent, or Firm* — Norton Rose Fulbright Canada LLP; Alexandre Daoust

(57) ABSTRACT

An orthotic foot brace for a person wearing a footwear, the orthotic foot brace comprising a leg holder, a foot strut having a hinge member extending from the posterior of the leg along a length of the footwear joining an instep strut securable to an instep portion of the footwear, and a heel member engaging the heel portion of the footwear below the hinge member, and a leg strut composed of a plurality of beams extending along the posterior of the lower leg towards the footwear, each beam secured at a first end within a cuff connector of the leg holder and secured at a second end within a foot strut connector of the foot strut.

4 Claims, 7 Drawing Sheets

(58) Field of Classification Search
CPC .... A43B 7/20; A43B 7/18; A43B 7/14; A43B 7/00
See application file for complete search history.

(56) References Cited

U.S. PATENT DOCUMENTS

| | | | | |
|---|---|---|---|---|
| 8,904,674 | B2 * | 12/2014 | Schwartz | A43B 7/20 36/89 |
| D804,044 | S | 11/2017 | Savard | |
| D875,960 | S | 2/2020 | Savard | |
| 11,141,302 | B1 * | 10/2021 | Franco | A43B 5/08 |
| 11,471,313 | B2 * | 10/2022 | Côté | A61F 5/0113 |
| 2016/0270943 | A1 * | 9/2016 | Forrey | A43B 7/20 |
| 2017/0296372 | A1 * | 10/2017 | Fay | A61F 5/0127 |
| 2018/0221187 | A1 | 8/2018 | Savard | |
| 2020/0113723 | A1 * | 4/2020 | Patterson | A61F 5/0113 |
| 2020/0206008 | A1 | 7/2020 | Côté | |

FOREIGN PATENT DOCUMENTS

| | | | |
|---|---|---|---|
| WO | 2017024382 | A1 | 2/2017 |
| WO | 2019046932 | A1 | 3/2019 |

* cited by examiner

_Fig. 1_

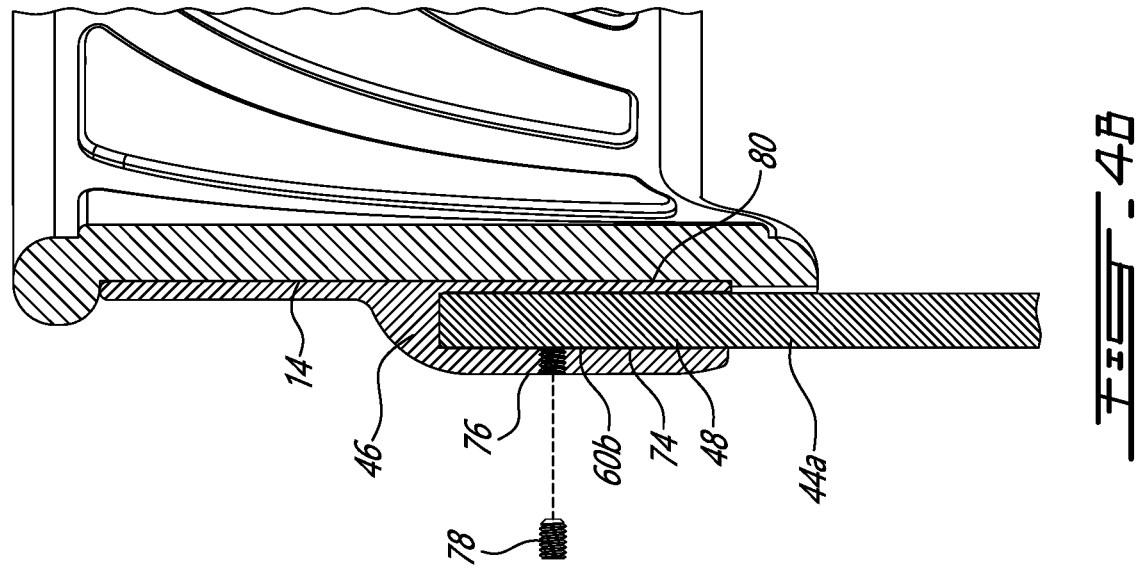
_FIG - 4B_
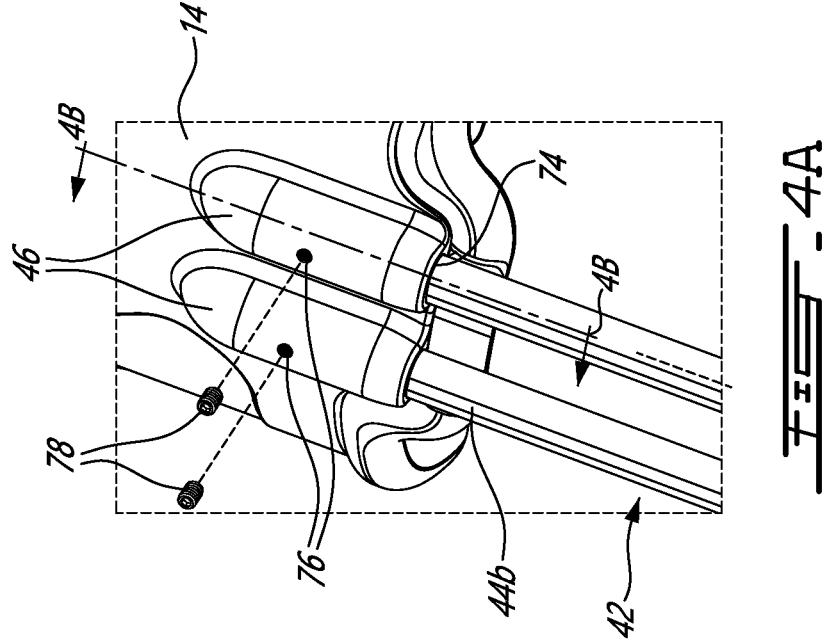
_FIG - 4A_

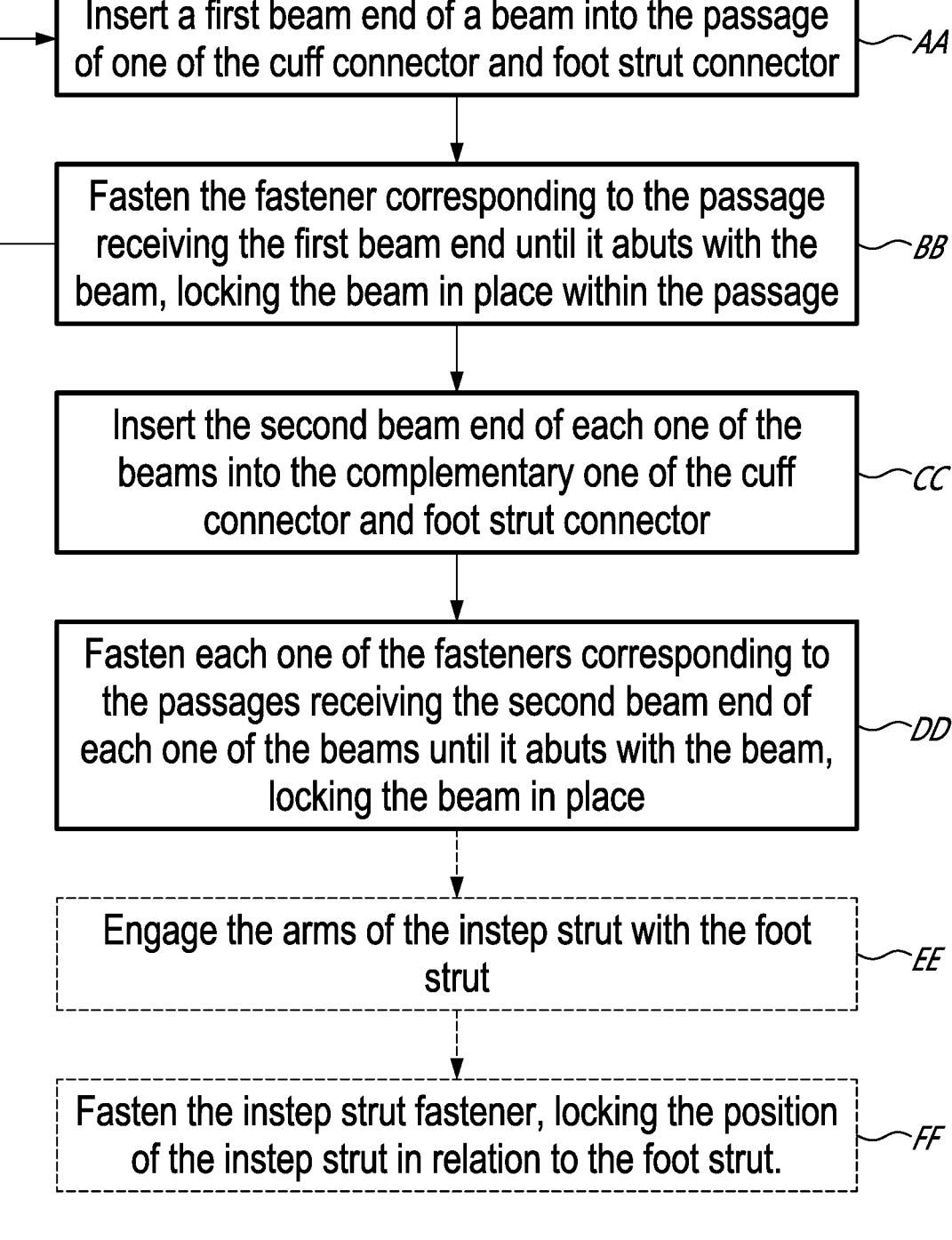

Insert a first beam end of a beam into the passage of one of the cuff connector and foot strut connector — AA Fasten the fastener corresponding to the passage receiving the first beam end until it abuts with the beam, locking the beam in place within the passage — BB Insert the second beam end of each one of the beams into the complementary one of the cuff connector and foot strut connector — CC Fasten each one of the fasteners corresponding to the passages receiving the second beam end of each one of the beams until it abuts with the beam, locking the beam in place — DD Engage the arms of the instep strut with the foot strut — EE Fasten the instep strut fastener, locking the position of the instep strut in relation to the foot strut. — FF

ORTHOTIC FOOT BRACE AND METHOD OF ASSEMBLY THEREOF

FIELD

The improvements generally relate to orthotics and, more particularly, to an orthosis for addressing a foot drop condition.

BACKGROUND

Foot drop or drop foot are terms which have been employed to describe ankle and toe dorsiflexor paresis (referred to hereinafter as foot drop for simplicity) resulting in the inability to raise the foot at the ankle, such that the foot inclines towards and scrapes the ground when walking. Dorsiflexion is the action of raising the foot, or more specifically the instep portion of the foot, upwardly towards the shin of a lower leg. This motion is one of the many actions that must take place during a normal gait cycle, and is particularly important through the entirety of the swing phase of the gait cycle, so that the toes of the foot (or more specifically for the toe section of the footwear being used) do not drag on the ground.

Many braces have been proposed to assist with or address the condition of foot drop. However, there always remains room for improvement.

SUMMARY

Orthotic foot braces can have a leg holder which attaches to the lower leg of a user and a foot strut which interfaces with a foot of the user. The leg holder can be interconnected to the foot strut via a leg strut. When a user enters the swing phase of the gait cycle with their foot exhibiting foot drop symptoms, the position of the lower leg and the orthotic food brace can transfer a force on the foot upwardly, towards the lower leg, via the leg holder anchoring point. The mechanical force transferred from the lower leg to the foot is provided by the leg strut, which mechanically unites the two pieces.

The leg strut is can be an elongated portion of the orthotic foot brace and play a role in the transfer of mechanical loads. While gaits may be ascertained in relation to a single plane coincident with a linear direction of travel of a user, it is understood that lower legs and foots go through complex multidirectional movements. The leg struts are not only subject to axial (applied along the longitudinal axis) and bending forces (applied orthogonal to the longitudinal axis), but further to torsional forces, which must effectively be transferred between the foot and the lower leg. Further, by the nature of the use of the orthotic foot brace, it can be desirable for the leg strut to be capable of operating in a cyclical way while minimizing fatigue failure. Weight, structural resistance, elastic behavior, and other design considerations of the leg strut are also factors to be taken into account. As the leg strut is an elongated member which forms a significant portion of the orthotic foot brace, the design of the leg strut can have a significant impact on the overall design.

It was found that providing a plurality of beams which extend alongside each other between the leg holder and the foot strut permitted to overcome at least some of the issues which have been associated to leg struts in orthotic foot braces. It was found that the plurality of beams can cooperate together to provide a significantly greater torsional resistance than either of them would otherwise exhibit individually, in addition to providing bending and axial resistance to the orthotic foot brace, in a way which can present a new options from the performance perspective (e.g. costs, weight, visual appeal, structural resistance).

It was further found that having certain elements of the orthotic food brace having an elasticity modulus larger than others brought about the advantage of increasing the efficiency of transferred forces and permits the bending of the foot strut to occur along the elements that are desired. It was determined that providing an instep strut made of a material which has an elasticity modulus higher than that of the foot strut to which it is connected permitted to reduce the amount of deflection of the instep strut, and therefore the amount of deflection of the foot attached thereto. It was found that this increased the efficiency of the mechanical forces transferred to the foot strut. Material with similar mechanical properties can be used for the leg strut, either alone or in combination with a corresponding material in the instep strut, such as to increase efficiency of the mechanical force transfer and encourage bending at the desired location of the orthotic foot brace.

In accordance with one aspect, there is provided an orthotic foot brace for a person wearing a footwear, the orthotic foot brace comprising a leg holder having a cuff securable to a lower leg of the person for use; a foot strut having a hinge member extending from the posterior of the leg along a length of the footwear joining an instep strut securable to an instep portion of the footwear, and a heel member engaging the heel portion of the footwear below the hinge member; and a leg strut composed of a plurality of beams extending along the posterior of the lower leg towards the footwear, each beam secured at a first end within a cuff connector of the leg holder and secured at a second end within a foot strut connector of the foot strut.

In accordance with another aspect, there is provided an orthotic foot brace for a person wearing a footwear, the orthotic foot brace comprising: a leg holder having a cuff securable to a lower leg of the person for use; a foot strut having a hinge member extending from the posterior of the leg along a length of the footwear, and a heel member engaging the heel portion of the footwear below the hinge member; an instep strut securable to an instep portion of the footwear and joining the foot strut at a lateral side of the footwear; and a leg strut extending along the length of the lower leg coupling the leg holder to the foot strut; wherein an elasticity modulus of a material of the instep strut is at least 2 times larger than a material of the foot strut.

In accordance with yet another aspect, there is provided a method of assembling an orthotic foot brace comprising a leg holder having a cuff, a foot strut having a hinge member extending from the posterior of the leg along a length of a footwear and joining an instep strut and a heel member engageable with the footwear, and a plurality of beams coupling the leg holder to the foot strut, the method comprising: Inserting a first beam end of a beam into a passage of one of a cuff connector and foot strut connector; fastening a fastener corresponding to the passage receiving the first beam end, the fastener abutting with a surface of the beam, locking the beam in place within the passage; repeating said inserting and fastening steps for a at least one subsequent beam; inserting, for each one of the beams, a second beam end into the other one of the cuff connector and foot strut connector; and fastening the fastener corresponding to the passage receiving the second beam end, the fastener abutting with the surface of the beam, locking the beam in place within the passage.

In this specification, the use of the terms anterior, posterior, plantar, dorsal, proximal, distal, medial, lateral make reference to the positions of elements with reference to the anatomical atlas which is centred at the trunk of the person. As such, distal denotes a region which is relatively furthest from the trunk of a person in contrast to another region said to be proximal, which denotes a portion that is relatively closer to the trunk of a person. Front generally refers to the space found facing the torso of a person and in the general direction that one would typically walk, while back generally refers to the space found facing the anatomical back of a person. As such, the anterior portion of the leg, for instance, refers to the general portion facing the direction of travel, while posterior is the portion facing away from the direction of travel. An imaginary median plane cuts the body longitudinally in half, where each one of the legs of a person is found in opposite sides of the median plane. As such, a medial portion of something refers to a portion which is closest or generally extending towards the median plane of the person, while the lateral portion refers to a portion which is furthest or generally extending away from the median plane. This is not to be confused with the expression lateral side(s) which can be either one of the sides of an object or subject.

In view of the nature of the orthotic foot brace of the present application, the anatomical reference terms may be used to denote relative positions of elements on the apparatus. These terms are to be understood in relation to the anatomical atlas of a hypothetical user who has his or her leg engaged within the orthotic foot brace. As will be made clear below, the orthotic foot brace of the present application can be used on either one or both feet of a user, which form a mirror image along the median plane. As such, the terms are not to be construed as limitative in any way and are to be used purely for the purpose of clarifying relative positions.

Many further features and combinations thereof concerning the present improvements will appear to those skilled in the art following a reading of the instant disclosure.

DESCRIPTION OF THE FIGURES

In the figures,

FIG. 1 is a front oblique view of an example of an orthotic foot brace;

FIG. 4A is a close-up oblique view of the portion 4A-4A of FIG. 3A;

FIG. 4B is a cross-sectional view taken along line 4B-4B of FIG. 4A;

FIG. 6 is a flow chart identifying steps for assembling an example orthotic foot brace;

DETAILED DESCRIPTION

Figure 2:
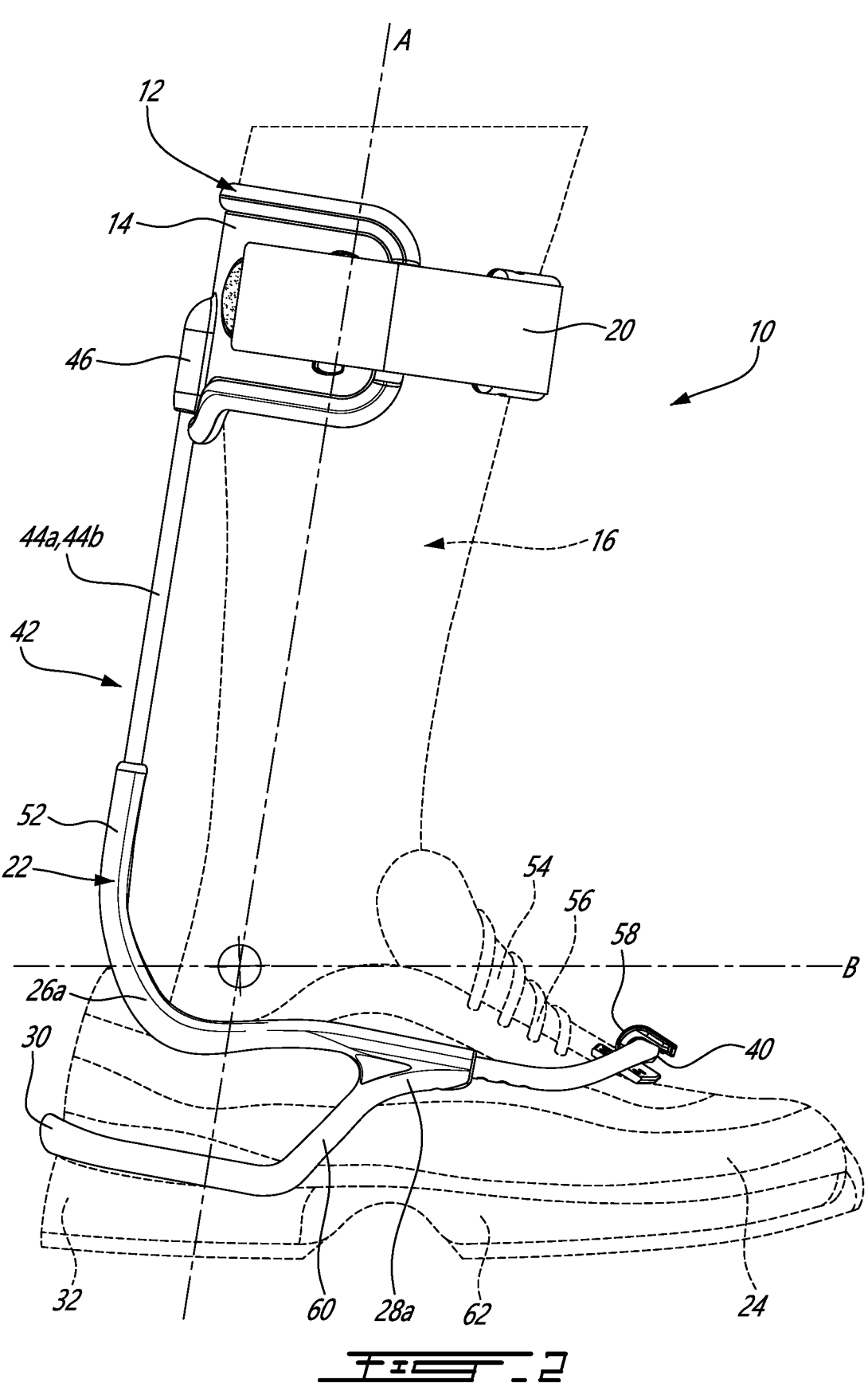
FIG. 2 is a lateral side view of another example of an orthotic foot brace coupled to a leg and foot of a user.

FIG. 1 shows an example of an orthotic foot brace 10. The foot brace 10 includes a leg holder 12 which has of a cuff 14 operable to attach to the lower leg of a user (See FIG. 2). In this embodiment, the leg holder 12 has a 18 which extends along the surface of the cuff 14 which receives the lower leg 16 of the user, and further includes a band 20 which extends from the first lateral side of the cuff 14 to an opposite lateral side of the cuff 14. In this particular case, the band 20 is hooked on the first side of the cuff 14 and is configured to extend over the anterior portion of the lower leg 16 and be fastened via a hook & loop fastener system. For instance, the fastening means can be of the type known as Velcro™, where the first one of the hook or loop portion is found on the band 20, while the other one of the hook and loop portion is provided on the cuff 14, such as to be able to secure the lower leg 16 against the pad 18.

It is understood that the particularities of the leg holder 12 may be altered without departing from the present disclosure. For instance, the band 20 may use other fastening means to hold the lower leg 16 in place. In another embodiment, the pad 18 can be altered or omitted without departing from the present disclosure.

Still referring to FIG. 1, the orthotic foot brace 10 further includes a foot strut 22 which is configured to interface with the foot of the user directly or indirectly via a footwear 24 (see FIG. 2). In this embodiment, the foot strut 22 generally extends downwardly from a single crest. Two hinge members 26a, 26b extend from the crest downwardly and forwardly until each one ultimately reaches a junction 28 28a, 28b. The junctions 28a, 28b form the connection with a heel member 30, which extends downwardly from the junction 28a, 28b and rearwardly under the hinge members 26a, 26b, back in the direction of the heel portion 32 of the footwear 24 (as shown in FIG. 2). Two proximal portions 34 of the heel member 30 extend from each one of the junctions 28a, 28b and merge at a distal portion 36, forming a loop between the two junctions 28a, 28b. The junctions 28a, 28b have an opening such as to receive the proximal portion of the arms 38a, 38b of an instep strut 40 therein. The instep strut 40 forming a crescent between the two arms 38a, 38b and bridging the two junctions 28a, 28b to one another, while extending forwardly from the junctions 28a, 28b of the foot strut 22.

The foot strut 22 and the leg holder 12 are joined by a leg strut 42. In this particular embodiment, the leg strut 42 has a pair of beams 44a, 44b. Each beam 44a, 44b has a first end engaged with the leg holder 12 and a second end engaged with the foot strut 22. The first end and the second end of the beams 44a, 44b can be identical in this embodiment.

As is perhaps best seen in FIG. 2, an orthotic foot brace 10 engaged with a lower leg 16 and footwear 24 of a user, the cuff 14 of the leg holder 12 is configured to abut with the posterior portion of the leg 16, while the band 20 is wrapped around the anterior portion of the leg 16. As will be discussed in further detail below with reference to FIGS. 4A and 4B, the cuff 14 includes a cuff connector 46, which receives a first end 48 of the beams 44a, 44b. The beams 44a, 44b extend downwardly and away from the cuff connector 46, along the posterior portion of the lower leg 16, and somewhat parallel to the longitudinal axis A of the leg. As is perhaps best seen in FIG. 3A, the orthotic foot brace has two beams, which are laterally spaced from one another, and extending in a parallel fashion along an axis C of the foot brace which is generally parallel to the axis A of the lower leg when the foot brace is in use.

Returning to FIG. 2, the beams extend from the cuff connector 46 until reaching the foot strut 22. The second end of the beams, engages the foot strut 22 via foot strut connectors 50a, 50b which are integrated to the crest 52 in this embodiment. The foot strut connectors 50a, 50b are located at the posterior of the leg 16, directly above the crest 52. The crest 52, which is also found at the posterior of the leg and foot, splits to form two hinge members 26a, 26b. These hinge members 26a, 26b extend downwardly from the crest 52 and forwardly along the longitudinal axis B of the footwear 24, while further extending along the lateral sides of the footwear 24. In this fashion, when the footwear 24 is engaged with the orthotic foot brace, as is perhaps best seen in FIG. 2, the hinge members 26a, 26b remain adjacent the lateral sides and general form of the footwear 24, while forming a curved portion which corresponds to the angle difference between the lower leg axis A and longitudinal axis B of the footwear 24.

Each one of the hinge members 26a, 26b end at a junction 28a, 28b approximately midway along the length of the footwear 24 and along the lateral sides of the footwear 24. An instep strut 40 is engaged with the junctions 28a, 28b at each one of the lateral sides, forming an extension to the hinge members 26a, 26b. The instep strut 40 extending from its connection at the junctions 28a, 28b along the longitudinal axis of the footwear B, into the instep portion 54 of the footwear 24 and extends over the dorsal section 56 of the footwear 24. A coupler 58 is used to secure the dorsal section 56 of the footwear 24 to the instep strut 40.

It is understood that, while the foot strut 22 in this embodiment is shown as having two hinge members 26a, 26b extending on each lateral side of the footwear 24 and each engaged with a respective arm 38a, 38b of the instep strut 40, the orthotic foot brace 10 can be altered without departing from the present disclosure. For instance, in an alternate embodiment, there can be only one arm to the instep strut which connects to either one of the junctions on the lateral side of the footwear. In such an embodiment, the instep strut extends from the engaged junction and terminates at the coupler. In yet another embodiment, the foot strut only has a hinge member on one lateral side of the footwear, whether it be the medial side or lateral side of a given footwear, and an instep strut extends on the same lateral side.

Still referring to FIG. 2, the foot strut 22 further includes a heel member 30 made integral to the foot strut 22 via the junction 28a, 28b. The heel member 30 has a proximal portion 60 which extends downwardly towards the plantar section 62 of the footwear 24 and then extends rearwardly under the hinge members 26a, 26b, laterally along the footwear 24 and proximal the plantar section 62 towards the heel portion 32. As with FIG. 1, the heel member 30 extends from the junction 28a at the first lateral side, around the heel portion 30 and terminates at the complementary one of the junctions 28b on the opposite lateral side.

As is perhaps best seen in FIG. 2, the heel member 30 follows the heel portion 32 and contributes to the mechanical work which can be transmitted between the foot and the orthotic foot brace 10.

As will be understood, the heel member 30 can be altered, replaced or omitted without departing from the present disclosure. For instance, in an alternate embodiment, the heel member may extend only from one of the lateral sides and terminates at the heel portion. In yet another embodiment, the heel member may extend from the crest of the foot strut towards the heel member and extends on one or both of the lateral sides of the footwear, proximal to the plantar section of the footwear. In yet another embodiment, the heel member is replaced entirely with a strap which extends over the dorsal section of the footwear between the two junctions found on the lateral side of the footwear, and provides corresponding support to the orthotic foot brace. In yet another embodiment, the heel member is omitted altogether.

Figures 3A, 3B, 3C:
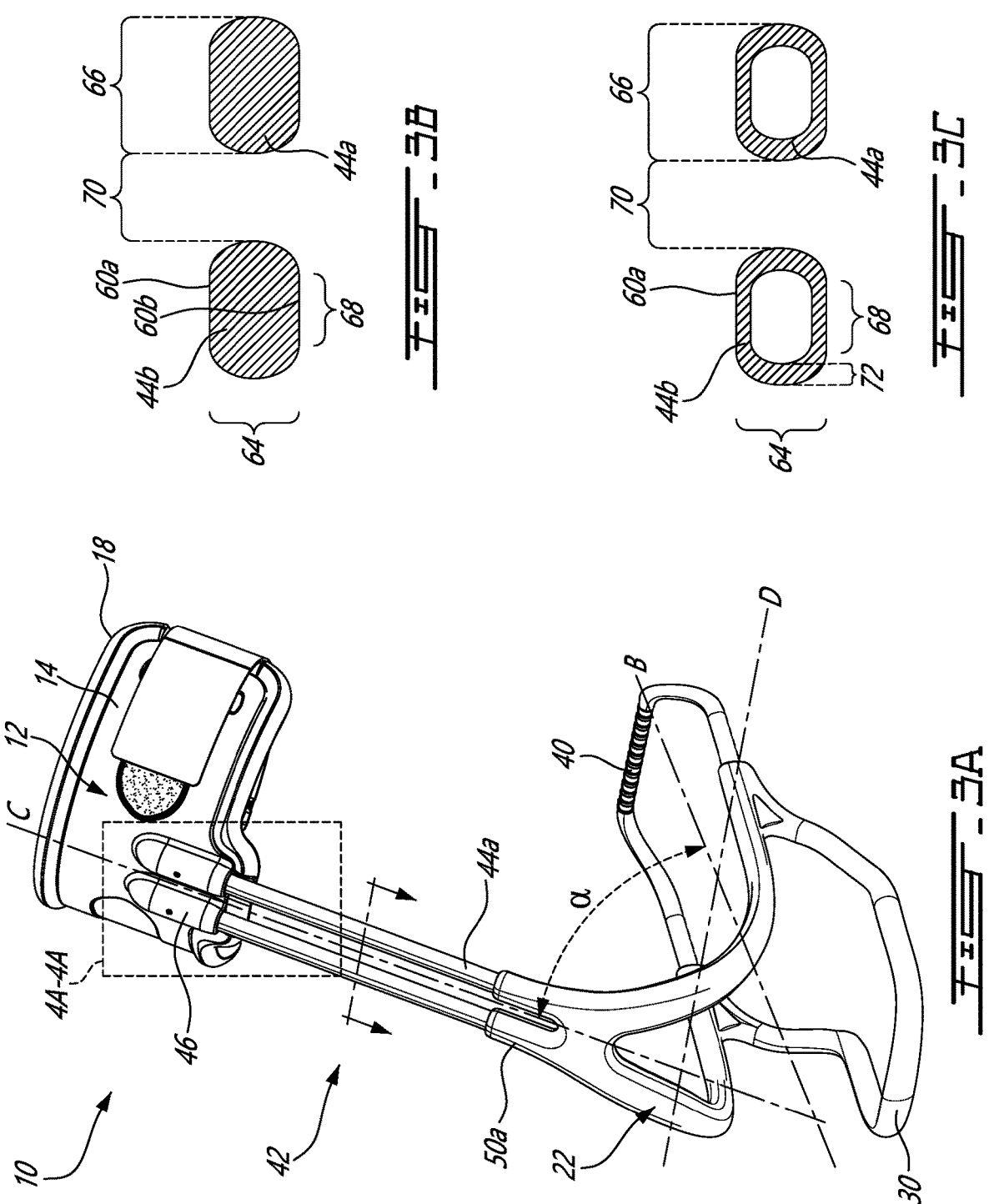
FIG. 3A is a back oblique view of the orthotic foot brace of FIG. 2 not coupled to a leg and foot of a user.
FIG. 3B a cross-sectional view taken along the line 3B-3B of FIG. 3A.
FIG. 3C is a cross-sectional view of an alternate embodiment of the beams of FIG. 3B.

Referring now to FIG. 3A, showing the orthotic foot brace 10 of FIG. 2 while not in use. It will be noted here that the orthotic foot brace 10 has two portions which extend generally along corresponding ones of two distinct longitudinal axes. The leg strut 42 extends along an axis C which, during use, is generally parallel to the axis A of the lower leg 16, and the instep strut 40 extends along axis B which corresponds to the longitudinal axis of the footwear 24. In contrast to the active use scenario presented in FIG. 2, the FIG. 3A forms a resting angle α which is acute, i.e. smaller than 90°. This angle can be any variety of values depending on the model and the needs of the client. When in use, however, as is perhaps best seen in FIG. 2, and depending on the step of the gait cycle which is to be observed, the angle between the axis C and the axis B is configured to change. As will be discussed below in more detail, in this example, it is desirable for the foot strut 22, and particularly the hinge member 26a, 26b to be of a material that has a modulus of elasticity lower than that of the leg strut and the instep strut, and to be the one which most significantly elastically deforms during use.

Still referring to FIG. 3A, in this embodiment, the beams 44a, 44b have a set of planar surfaces extending along the beam length. As is perhaps best seen in FIG. 3B showing a cross-section of the pair of beams along the line 3B-3B of FIG. 3A, the beams are obround, or otherwise said, have a "racetrack" cross-sectional shape. The planar surfaces 60a, 60b of the beams 44a, 44b are circumferentially opposed to one another, such as to form parallel planes interspaced by the curved surfaces on each side.

In the particular embodiment illustrated in FIG. 3B, the beams 44a, 44b are filled. The beams 44a, 44b, can be said to have an outer radius 62 corresponding to the curved faces. The beams further having a beam thickness 64, a beam width 66, a planar surface width 68 which is smaller than the beam width 66 due to the presence of the curved faces, and a beam spacing 70, between the beams 44a, 44b. Depending of the embodiment, the exact size and dimensions of the beams 44a, 44b can be defined by any combination of these measurements.

It is understood that the exact structure and dimensions of the beams 44a, 44b can be altered without departing from the present disclosure. For instance, FIG. 3C shows an alternate embodiment of the beams 44a, 44b which can be used with the foot brace 22 in FIG. 3A. In this embodiment, the beams 44a, 44b are very similar to the beams of FIG. 3B, except that they are hollow rather than being full. A wall thickness 72 of a peripheral wall of the beams 44a, 44b delimits an internal cavity.

It is understood that different mechanical properties can be achieved by changing the structural values of the beams, no matter whether they are solid, such as shown in FIG. 3B or hollow, such as shown in FIG. 3C. For instance, the variable to modified to achieve the desired mechanical property can be the beam thickness, beam width, outer radius, planar surface width etc. It also understood that different mechanical properties can be achieved by adjusting the the beam spacing. As is perhaps best seen in FIG. 3A, the beams 44a, 44b couple the leg holder 12 to the foot strut along the axis C. They can be subject to axial and bending stresses, but also to torsional stresses. The beam spacing 70 can be chosen to provide the desired torsional strength of the assembly forming the leg strut 42. As will be further discussed below, in this embodiment, the non-circular cross-section of the beams at the cuff connector 46 and foot connector 50a, 50b also provides means to impede eventual slippage between the beams and connectors, helping in ensuring that the structure formed by the beams and the connectors acts in an integral manner when subjected to torsion.

It is understood that the exact dimensions, internal structure and surface structures of the beams can be altered without departing from the present disclosure. For instance, in an alternate embodiment, the beams only have a single planar surface. In yet another embodiment, the curved surface may be omitted. In yet another embodiment, the planar surfaces of the beams may only extend from the beams ends (FIG. 4B) for a portion of the beam length whereas the remaining length of the beam may be circular or oval.

The beams can be made of any material deemed suitable for the application of the foot brace. In this particular embodiment, the beams are made of carbon fiber finished graphite. In certain embodiments, the beams can be dimensioned to provide a beam flexural modulus of approximately 1.5 GPa at room temperature, for instance. In alternate embodiments, the beams are made of a material which mechanical properties corresponding to those of the instep strut, described here below in detail. In yet another embodiment, the beams are made of the same material as the instep strut.

Returning to FIG. 3A, in this embodiment, the two planar surfaces 60a, 60b of the beams 44a, 44b are oriented such that the first one of the planar surfaces faces the posterior portion of the lower leg when in use, while the opposite planar surface faces away the lower leg. This can bring the advantage of minimizing the chances that the user's leg rubs against the beams while further providing an accessible flat surface for fasteners to securely engage against, as will be discussed in further details below.

The beams 44a, 44b couple the leg holder 12 to the foot strut 22 via the cuff connector 46 and the foot strut connector 50a, 50b, respectively. Attention is now brought to FIG. 4A which shows a close-up view of the section 4A-4A of the orthotic foot brace 10 of FIG. 3A. A cuff connector 46 is available to receive and engage with the end 48 of each one of the beams 44a, 44b. The beams 44a, 44b are received within the cuff connector 46 via corresponding passage openings which lead to respective passages 74. The passages each have a cross-section shape and size matching the shape and size of the cross-section of the beams 44a, 44b, so as to securely receive the body of the beam while minimizing movement.

As was described above, in this embodiment, a planar surface 60b of the beams 44a, 44b are oriented away from the posterior portion of the leg of a user. The cuff connector has fastener apertures 76 configured to receive a corresponding fastener 78 therein. As is perhaps best seen in FIG. 4B, showing a cross-sectional view of the cuff connector 46 and the beams 44a, 44b received therein along line 4B-4B in FIG. 4A, the fastener aperture 76 communicates with the passage 74 and is aligned with the planar surface 60b of the beams 44a, 44b. As such, when the fastener 78 is received within the fastener aperture 76, the tip of the fastener 78 can abut flatly against the planar surface 74 of the beam 44a and force the beam 44a against the opposing face 80. The fasteners 78 can collaborate with the tight fitting of the non-circular shapes of the beams 44a, 44b and their respective passages 74 in preventing the rotation of the beams 44a, 44b in their respective passages 74.

In this manner, the cuff connector 46 transfers forces efficiently to the beam. This ensures that the load is evenly distributed along the surface of the beam end which is received within the cuff connector passage, while avoiding relative rotation between the beam and the cuff connector. The combination of the structure of the passage of the cuff connector, in combination with the structure of the beams and means of frictionally holding the beams in place permit the cuff and the beams to work together to efficiently transfers axial, bending and torsional forces.

Figures 4C, 5:
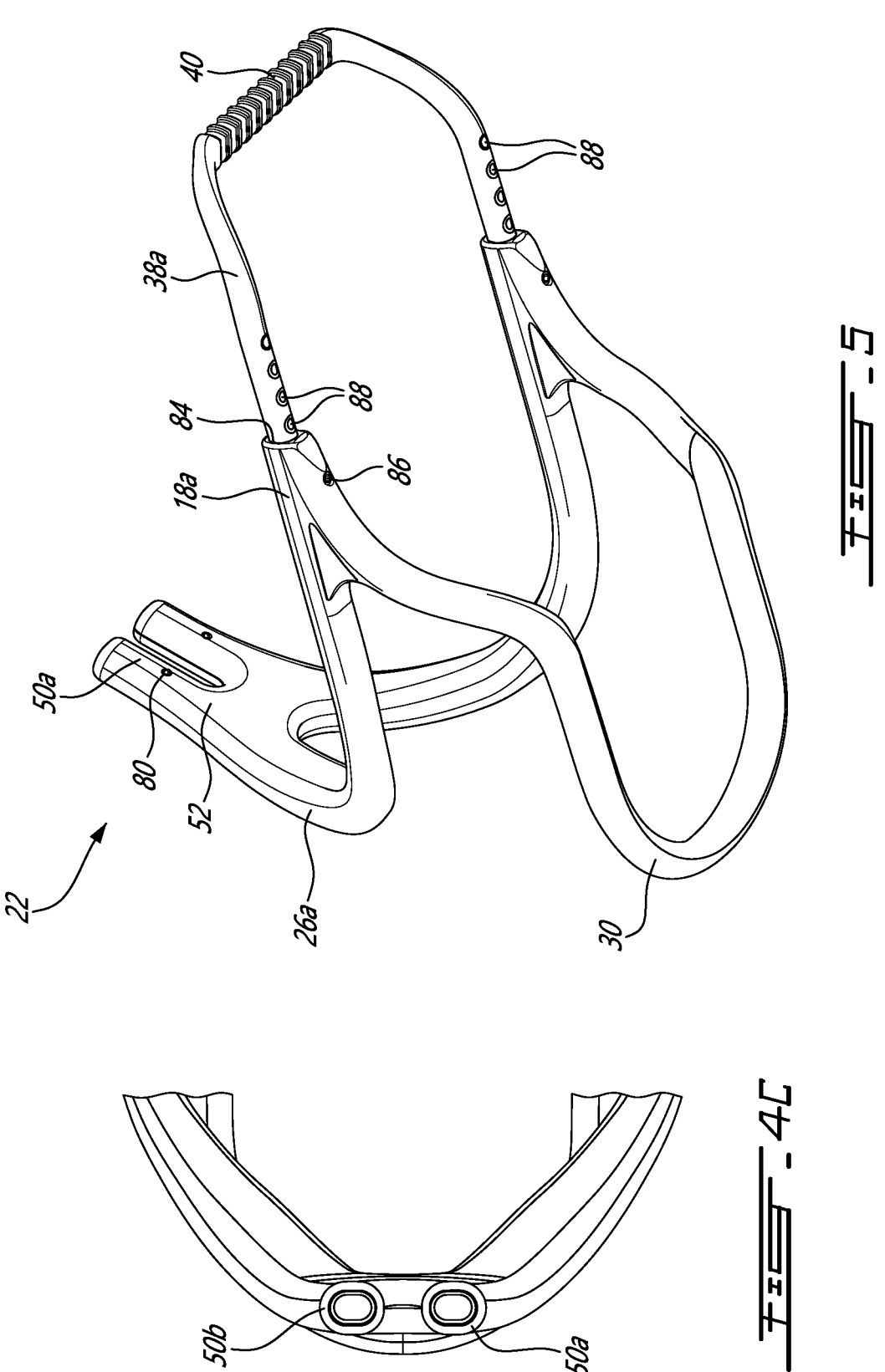
FIG. 4C is a partial top view of the foot strut taken along a cross-section of the beams.
FIG. 5 is a bottom oblique view of an example of an orthotic foot brace, without the beams and leg strut.

As is perhaps best seen in FIG. 4C, the foot strut connectors which receive the opposite end of the beams have a similar structure and mode of operation in this embodiment, except that in this specific embodiment, the fasteners apertures 80 of the foot strut connectors 50a, 50b face towards the leg as opposed to the fastener apertures 76 of the cuff connector 46 which faces away from the leg.

In this particular example, the fasteners are headless fasteners which are capable of having their entire body received within the fastener apertures of the cuff connector and foot strut connector. This avoids having a fastener head which may rub with a user's leg or hook with clothing, for instance. It will be understood that other fastening means may be used without departing from the present disclosure. For instance, while the embodiment discussed above disclosed a single fastener for each one of the cuff connectors and foot strut connectors, it may be desirable to have two fasteners for each one of the connectors. In an alternate embodiment, there is fastener apertures and corresponding fasteners facing the posterior portion of the lower leg of a user for both the foot strut connector and the cuff connector as well as fastener apertures and corresponding fasteners facing away from the posterior portion of the lower leg of a user, effectively providing two fasteners for engagement of the beam at each one of the connectors of the orthotic foot brace. In yet another embodiment, the fastener is configured to extend through the beam received within the connector. In yet another embodiment, the beams can be adhered to, or manufactured integrally with, the cuff connector and/or the foot strut connector.

It will be understood that the cuff connector and the foot strut connectors can be altered without departing from the present disclosure. For instance, the cross-sectional shape of the beam may be altered such as to have only a single planar surface. In such an alternate embodiment, the cross-section of the cuff connector and foot strut connector passages would be adapted to correspond to that of the beam. In this same embodiment, it may be desirable for the fastener aperture and the fastener to be placed on the same side of the orthotic foot brace (ie. either facing towards or facing away from the posterior portion of the lower leg of a user) and this side may correspond to the orientation of the planar surface of the beam.

Still referring to FIG. 5, the junctions 18a, 18b of the foot strut 22 each have an opening 84 capable of receiving a corresponding arm 38a of the instep strut 40. As the instep strut 40 engages the instep portion of the footwear 24 which may vary in dimension from one user to another, the instep portion of the orthotic foot brace is configured to be adjustable along the length of the footwear 24. This is provided by the sliding of the arms 38a, 38b of the instep strut 40 within the junctions 18*a*, 18*b*, providing a certain level of adjustability to the user. The instep strut 40 can be held firmly in place via the use of an instep strut fastener 86 which can be secured in a corresponding fastener aperture formed in the junctions 18*a*, 18*b*. The instep strut fastener 86 can be loosened to permit the longitudinal sliding motion of the instep strut arms 38*a*, 38*b* along the footwear length, and tightened in a way for the instep strut fastener 86 to engage with adjustment depressions 88 provided on the instep strut arms 38*a*, 38*b*. When the instep strut fastener 86 is tightened, it engages with a corresponding depression, locking the instep strut 40 in the desired position.

It is understood that other adjustment and fastening means of the instep strut may be provided without departing from the present disclosure. For instance, in an alternate embodiment, the arms of the instep strut have apertures for receiving a portion of the instep strut fastener for engagement instead of an adjustment depression. In yet another embodiment, the instep strut can be made to have no depressions and is configured to engage within the junction of the foot strut in the same manner the beams are engaged with the foot strut connector or cuff connectors. In yet another embodiment, the instep strut arms are permanently engaged at the junction of the foot strut and provide no adjustability.

Attention is now brought to FIG. 6 showing a flow chart identifying steps for assembling an example orthotic foot brace. The different elements of the orthotic foot brace discussed above can be provided separately, such as to permit saving space during transportation and storage, and can be assembled to provide the orthotic foot brace via the following steps.

At step AA, a beam is to be engaged with either one of the cuff and foot strut by inserting a beam end into the passage of one of the cuff connectors and foot strut connectors. Once the beam is snuggly received within the given passage, it is to be locked in place via the fastener. At step BB, the fastener corresponding to the passage having received the beam end is fastened until it abuts with the beam, locking it in place. As the embodiment of the orthotic foot brace includes two beams, steps AA and BB are repeated with the first end of another beam, such as to have two beams which have a first end received within a connector.

It is understood that each one of the two beams can have their first end engaged with the same connector of the orthotic foot brace (ie. both connected to the foot strut or the cuff). Yet, in alternate embodiments, each one of the beams has a first end engaged to different connectors. Written otherwise, the first beam has its first end engaged with the cuff connector of the cuff, while the subsequent beam has its first end engaged to the foot strut connector of the foot strut or vice versa.

Still referring to FIG. 6, at step CC the second beam end of each one of the beams is inserted into the complementary one of the cuff connectors and foot strut connectors passages and subsequently locked in place via the corresponding fasteners at step DD.

In some embodiments, it may be desirable for the instep strut to arrive disassembled from the foot strut. In such embodiments, the arms of the instep strut are to be received within the openings found at the junctions of the foot strut and fastened in place via the instep strut fasteners at steps EE and FF, respectively.

Figure 8:
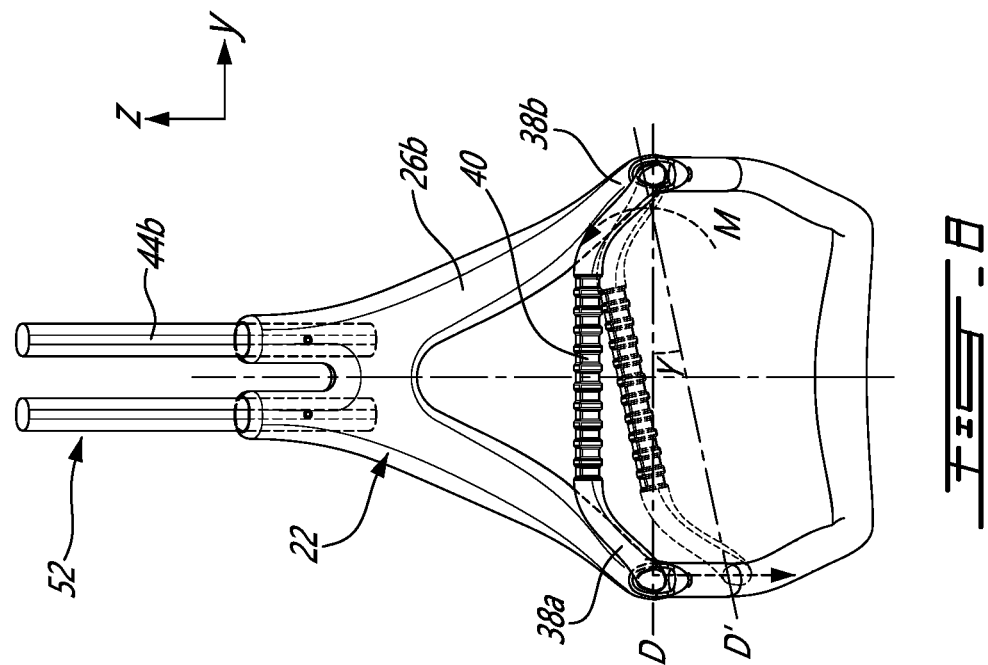
FIG. 8 is a partial front view of an example orthotic foot brace being loaded on one of the lateral or medial side and deflecting under load.
Figure 7:
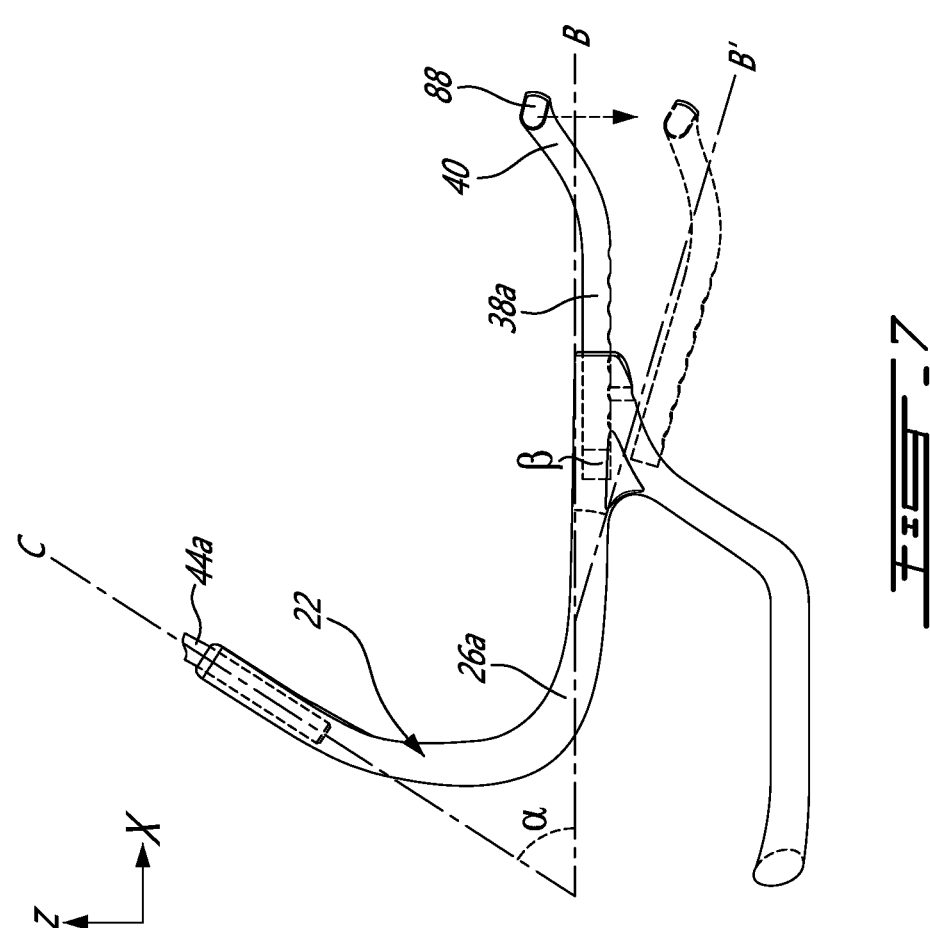
FIG. 7 is a partial side view of an example orthotic foot brace being loaded uniformly on the lateral and medial sides and deflecting under load.

FIG. 7 shows a partial side view of an example orthotic foot brace 10 being loaded uniformly on the lateral and medial sides and deflecting under load. FIG. 8 shows is a partial front view of the orthotic foot brace being loaded on the lateral side.

During use, the orthotic foot braces transfer loads from the footwear of the patient's foot suffering from foot drop to the rest of the brace. In order to offer an increased efficiency, it is desirable to minimize the amount of unpredictable and undesirable deflection which may occur via certain elements of the orthotic foot brace 10. This is particularly the case for the instep strut 40 which is the primary point of force transfer between the footwear 24 and the orthotic foot brace 10.

For clarity purposes, FIGS. 7 and 8 demonstrate loading scenarios which are applied in theoretically perfect planes and applied as point loads on the orthotic foot brace 10, solely for the purpose of demonstration. In both these scenarios, it is understood that the beams 44*a*, 44*b* are held static and are capable of providing any necessary reaction forces to the foot strut in order to exemplify the deflection of the instep strut 40, such as is the case when the user wears the orthotic foot brace 10. Further, for the purposes of identifying different lateral side elements, the orthotic foot brace in these figures is expected to be of use with the right foot of a user. As such, a lateral arm 30*a* of the instep strut is found on the left-hand side of FIG. 8, while a medial arm 30*b* of the instep strut is found on the right-hand side of FIG. 8.

In FIG. 7, a load is applied downwardly in the x-z plane at the distal portion 88 of the instep strut 40. It is applied in such a way that the bending is perfectly distributed between both the lateral arm 38*a* and the medial arm 38*b* of the instep strut 40. Given the mirrored structure of the orthotic foot brace 10 along the plane formed by axes C & B, perhaps best seen in FIG. 3A, the instep strut 40 exhibits equal deflection along both of its lateral sides. In FIG. 8, a load is applied downwardly in the y-z plane at the contact point between the lateral arm 38*a* of the instep strut 40 and the foot strut 22. This load mimics a scenario where the instep strut 40 is subject to a moment M along the y-z plane which may be brought upon by the rotation of the user's foot.

Attention is first brought to FIG. 7. When a patient lifts his foot, the instep strut 40 engaged with the dorsal section of the footwear is subject to a downwards load provided by the user's inability to raise his or her foot at the ankle. It is desirable for the instep strut to be engaged with the foot far enough to create a large moment arm from a pivot point, however, as the length of the instep strut 40 is increased so is the deflection of the material when loaded. For efficiency purposes, it is desirable for the instep strut 40 to transfer as much of the load to the foot strut 22, such as to permit the hinge members 26*a*, 26*b* to deflect in a predictable and desirable fashion, providing a deflection angle β between the resting instep strut along axis B and the loaded instep strut along the axis B'. The deflection angle β in this embodiment is provided by the deflection of the foot strut 22 via the transfer of loads from the instep strut 40.

Having this in mind, the instep strut 40 and the foot strut 22 are made of different materials. The instep strut 40 is made of a fiber reinforced polymer, preferably a glass reinforced long chain polyamide resin. It will be understood that any other type of reinforced polymer can be used without departing from the present disclosure. For instance, the said reinforced polymer can having fibers of different materials therein, such as glass, carbon, aramid or basalt. The foot strut 22, on the other hand, is made of a thermoplastic elastomer, preferably a thermoplastic polyester elastomer. It will be understood that other types of thermoplastic elastomers can be used without departing from the present disclosure. For instance, thermoplastic polyolefinelastomers, thermoplastic vulcanizates, thermoplastic polyurethanes, thermoplastic copolyester, thermoplastic polyamides or even not classified thermoplastic elastomers can be used.

In all cases, the material of the instep strut 40 provides an elasticity modulus which is at least 2 times larger than that of the material of the foot strut, preferably at least 5 times larger and even more preferably at least 12 times larger. The material of the instep strut preferably an elasticity modulus of at least 14 GPa, and the material of the foot strut preferably has an elasticity modulus of no more than 1.5 GPa. It is understood that the mechanical properties of the materials are to be taken at room temperature, preferably at room temperature and that the elasticity modulus of interest for these elements is the flexural modulus. In this particular embodiment, the material of the instep strut is a glass reinforced long chain polyamide resin having a flexural elasticity modulus of approximately 14.4 GPa at 23° C., whereas the material of the foot strut is a thermoplastic polyester elastomer having a flexural elasticity modulus of approximately 1.12 GPa at 23° C.

Still referring to FIG. 7 and for the sake of completeness, an example angular deflection of the instep strut when subject to a load is provided. In this embodiment, when the load applied to the distal portion of the instep strut corresponds to a 2.75 Kg weight (ie. the force applied corresponds approximately to 26.97 Newtons), the instep strut angularly deflects from its original resting position along axis B, to a loaded position along axis B'. In this example, the angular deflection β of the instep strut is of no more than 12°.

Attention is now brought to FIG. 8. During use, the user's foot is subject to rotations, typically called medio-lateral rotations, which are equally as important to support as the dorsiflexion (FIG. 7) of the foot. For efficiency purposes, it is desirable for the instep strut to transfer as much as the load to the foot strut, such as to permit the hinge member to deflect in a predictable and desirable fashion, providing a lateral angular deflection γ between the axis D, crossing corresponding portions of the lateral and medial arms of the instep strut when resting (unloaded), and the axis D' of the instep strut when laterally loaded. The orthotic foot brace in this embodiment has corresponding material and elasticity moduli as those having been described in FIG. 7. For the sake of conciseness, these materials and elasticity moduli will not be repeated.

Still referring to FIG. 8, and for the sake of completeness, an example lateral angular deflection of the instep strut when subject to a lateral load is provided. In this embodiment, when the load applied at the contact point of the lateral arm 38a with the foot strut 22 corresponds to a 2.75 Kg weight (ie. the force applied correspond approximately to 26.97 Newtons), the lateral arm 38a angularly deflects from its original resting position forming the axis D which traverses the lateral and the medial arm of the instep strut, to a loaded position forming the axis D'. In this example, the lateral angular deflection γ of the instep strut is of no more than 14°.

While FIG. 7 and FIG. 8 shows two possible loading conditions, it is understood that the orthotic foot brace will be subject to complex, multidirectional loading conditions during use. However, in all cases, the present embodiment permits the loads from the instep strut to be efficiently transferred to the foot strut, which is the body providing the majority of the deflection. In this example, when the instep strut is subject to a load, at least 80% of the deflection encountered between the lower leg (ie. axis A, parallel to the axis C during use) and the instep strut (ie. pivot of axis B about an axis parallel to axis D) is provided by the hinge members of the foot strut, preferably at least 80% of the deflection is provided by the hinge members, more preferably at least 85% of the deflection is provided by the hinge members, more preferably at least 90% of the deflection is provided by the hinge members, even more preferably at least 95% of the deflection is provided by the hinge members and even more preferably at least 99% of the deflection is provided by the hinge members.

Similarly, when the instep strut is subject to a load, at least 80% of the deflection encountered between the lateral arm and the medial arm of the instep strut (ie. pivot of axis D about an axis parallel to axis B) is provided by the hinge members of the foot strut, preferably at least 80% of the deflection is provided by the hinge members, more preferably at least 85% of the deflection is provided by the hinge members, more preferably at least 90% of the deflection is provided by the hinge members, even more preferably at least 95% of the deflection is provided by the hinge members and even more preferably at least 99% of the deflection is provided by the hinge members.

It is understood that corresponding material and elasticity moduli as those having been described in FIG. 7 and FIG. 8 can be used for the leg strut of the orthotic foot brace, to provide corresponding mechanical advantages.

The examples described above and illustrated are intended to be exemplary only. Many further features and combinations thereof concerning the present improvements will appear to those skilled in the art. The scope is indicated by the appended claims.

What is claimed is:

1. An orthotic foot brace for a person wearing a footwear, the orthotic foot brace comprising:
    a leg holder having a cuff securable to a lower leg of the person for use;
    a leg strut extending from the leg holder;
    an instep strut having a coupler for attachment to a dorsal section of the footwear during use, two arms, and two ends, each one of the two arms extending rearwardly from the coupler, to a corresponding one of the two ends;
    a foot strut having two hinge members, a heel member and two junctions, each hinge member extending downwardly and forwardly from the leg strut until each one reaches a corresponding one of the two junctions, on a corresponding side of the user's foot during use, the two junctions forming a structural connection with the heel member, the heel member having two proximal portions, each one of the two proximal portions extending downwardly and rearwardly from a corresponding one of the two junctions and merging with the other one of the two proximal portions at a distal portion, forming a loop between the two junctions, the distal portion being engaged with a heel portion of the footwear during use, each one of the two junctions having an opening receiving a corresponding one of the two ends of the two arms of the instep strut, the instep strut forming a crescent between the two arms and bridging the two junctions to one another while extending forwardly from the two junctions; wherein the foot strut and the heel member form part of a same component made of a same material extending continuously across the two junctions between the foot strut and the heel member.

2. The orthotic foot brace of claim 1 wherein the same material is a thermoplastic elastomer.

3. The orthotic foot brace of claim 1 wherein the instep strut is made of a fiber-reinforced polymer.

4. The orthotic foot brace of claim 1 wherein the instep strut is made of glass-reinforced long chain polyamide resin.

* * * * *